United States Patent
De Bonis et al.

(10) Patent No.: US 11,576,780 B2
(45) Date of Patent: Feb. 14, 2023

(54) ARTICULATED PROSTHESIS FOR A TRICUSPID OR MITRAL VALVE AND RELATED CATCHING DEVICE

(71) Applicant: STAR TRIC S.R.L., Milan (IT)

(72) Inventors: Michele De Bonis, Cernusco sul Naviglio (IT); Elisabetta Lapenna, Cernusco sul Naviglio (IT); Ottavio Alfieri, Brescia (IT); Federico Pappalardo, Milan (IT); Angelo Passanante, Milan (IT)

(73) Assignee: STAR TRIC S.R.L., Milan (IT)

( * ) Notice: Subject to any disclaimer, the term of this patent is extended or adjusted under 35 U.S.C. 154(b) by 0 days.

(21) Appl. No.: 16/613,498

(22) PCT Filed: May 3, 2018

(86) PCT No.: PCT/IB2018/053074
§ 371 (c)(1),
(2) Date: Nov. 14, 2019

(87) PCT Pub. No.: WO2018/211346
PCT Pub. Date: Nov. 22, 2018

(65) Prior Publication Data
US 2020/0163757 A1   May 28, 2020

(30) Foreign Application Priority Data

May 16, 2017   (IT) .................. 102017000052909

(51) Int. Cl.
*A61F 2/24* (2006.01)

(52) U.S. Cl.
CPC ...... *A61F 2/246* (2013.01); *A61F 2220/0016* (2013.01); *A61F 2220/0025* (2013.01);
(Continued)

(58) Field of Classification Search
None
See application file for complete search history.

(56) References Cited

U.S. PATENT DOCUMENTS

| 2002/0013571 A1 | 1/2002 | Goldfarb et al. |
| 2004/0049207 A1* | 3/2004 | Goldfarb ................ A61F 2/246 606/139 |

(Continued)

FOREIGN PATENT DOCUMENTS

| WO | WO-2004103162 A2 | 12/2004 |
| WO | WO-2018211346 A1 | 11/2018 |

OTHER PUBLICATIONS

International Search Report and Written Opinion for International Application No. PCT/IB2018053074, dated Jul. 24, 2018, European Patent Office, Netherlands, 12 pages.

*Primary Examiner* — Leslie Lopez
(74) *Attorney, Agent, or Firm* — Sterne, Kessler, Goldstein & Fox P.L.L.C.

(57) ABSTRACT

An articulated prosthesis, left in the patient's heart for repairing a tricuspid or mitral valve, is conceived so as to grip simultaneously all the three leaflets of the tricuspid valve, or the two of the mitral valve, so as to make them lay distended fully in the valve plane and assume a final configuration as in the common surgical procedure. It is also disclosed a related catching device and a device for repairing a tricuspid or mitral valve.

2 Claims, 14 Drawing Sheets

(52) U.S. Cl.
CPC ............... *A61F 2220/0041* (2013.01); *A61F 2220/0091* (2013.01); *A61F 2250/0008* (2013.01)

(56) References Cited

U.S. PATENT DOCUMENTS

| | | | |
|---|---|---|---|
| 2005/0273135 A1* | 12/2005 | Chanduszko | A61B 17/0057 606/213 |
| 2007/0080188 A1 | 4/2007 | Spence et al. | |
| 2014/0005778 A1* | 1/2014 | Buchbinder | A61F 2/2412 623/2.18 |

* cited by examiner ively related to the central part of the free edges of the free edges of the tricuspid leaflets, producing a 'clover'-shaped valve. A pictorial representation of a tricuspid valve treated according to this technique is depicted in FIG. 1. Clinical results obtained with this technique are reported in:

ARTICULATED PROSTHESIS FOR A TRICUSPID OR MITRAL VALVE AND RELATED CATCHING DEVICE

TECHNICAL FIELD

This disclosure relates to the repair of heart valves exhibiting valve regurgitation. More particularly, the invention relates to an apparatus suitable for a less invasive repair of a heart valve using an articulated prosthesis of a catching device, deliverable through a catheter, for leaflets of a tricuspid or mitral heart valve.

BACKGROUND

The most common type of tricuspid valve disease is functional tricuspid regurgitation (TR), which is mainly due to the dilatation of the tricuspid annulus secondary to right ventricular enlargement. Later in the course of the disease, tethering of the tricuspid leaflets may also occur because of the displacement of the papillary muscles inside the right ventricle. When functional TR is due to both severe annular dilatation and leaflet tethering, annuloplasty alone is unlikely to be successful. Similarly, TR caused by prolapse or flail of multiple leaflets, as typically seen in post-traumatic and severe degenerative TR, cannot be rectified by a simple annuloplasty procedure.

In order to achieve an effective and durable repair, the so-called 'clover technique' has been proposed. This technique consists in suturing together the central part of the free edges of the tricuspid leaflets, producing a 'clover'-shaped valve. A pictorial representation of a tricuspid valve treated according to this technique is depicted in FIG. 1. Clinical results obtained with this technique are reported in:

"*The 'clover technique' as a novel approach for correction of post-traumatic tricuspid regurgitation*", O. Alfieri, M. De Bonis et al., Journal of Thoracic and Cardiovascular Surgery, 2003; Vol. 126, No. 1, pages 75-79;

"*A novel technique for correction of severe tricuspid valve regurgitation due to complex lesions.*" De Bonis M, Lapenna E et al. Eur. J. Cardiothorac. Surg. 2004 May; 25(5):760-5.

"*Four-leaflet clover repair of severe tricuspid valve regurgitation due to complex lesions*", E. Lapenna, M. De Bonis et al., Journal of Cardiovascular Medicine, 2008, Vo. 9 No. 8, pages 847-849;

"*The clover technique for the treatment of complex tricuspid valve insufficiency: midterm clinical and echocardiographic results in 66 patients*", E. Lapenna, M. De Bonis et al., European Journal of Cardiothoracic Surgery, 37 (2010), 1297-1303;

"*Long-term results (up to 14 years) of the clover technique for the treatment of complex tricuspid valve regurgitation*", De Bonis M, Lapenna E, et al. Eur. J. Cardiothorac. Surg. 2017 Feb. 23. doi: 10.1093/ejcts/ezx027.

A device for catching valve leaflets of a mitral valve as well as of a tricuspid valve, is marketed with the commercial name MITRA CLIP™. This prior device, that can be introduced into the heart through a catheter by a vascular approach or throughout a small incision in the chest, comprises a fastener applicator of the type shown in FIG. 2. The sequence of operations to be performed for implanting a MITRA CLIP™ fastener is shown in FIG. 3. In the depicted case the heart valve is the mitral valve, though the same observations hold mutatis mutandis also for the tricuspid valve. Using a catheter, the MITRA CLIP™ fastener is inserted in a folded configuration into the heart; when the catheter is close to the heart valve, the fastener is deployed like an umbrella to catch the leaflets of the valve, and it is subsequently closed to grip the leaflets together. Finally, the MITRA CLIP™ fastener is left closed in the heart for keeping the leaflets together, thus reducing valve regurgitation.

SUMMARY

Unfortunately, tests carried out by the applicant have shown that this prior applicator with two arms is unable to catch simultaneously all the 3 leaflets of the tricuspid valve and, therefore, its efficacy in treating tricuspid regurgitation is very limited. In presence of very dilated tricuspid annulus, catching also of just 2 leaflets of the tricuspid valve is rather difficult with the MitraClip™ system. When more MitraClips™ are implanted in the aim of improving the competence of the tricuspid valve, the risk of tricuspid stenosis significantly increases by reducing too much the light of the repaired tricuspid valve. Without being bound to a theory, the increased risk of stenosis may be due to the fact that the central portions of the leaflets of the heart valve are folded at a right angle in respect to the plane of the heart valve in order to be gripped together one against the other. The leaflets assume an unnatural configuration overstretched toward the center of the valve plane, thus the light therebetween is reduced and the risk of stenosis is increased.

In order to prevent this problem, the device of the present disclosure is conceived so as to grip simultaneously all the three leaflets of the tricuspid valve, or the two of the mitral valve, so as to make them lay distended fully in the valve plane and to assume a final configuration as in the common surgical procedure.

This outstanding result is attained with an articulated prosthesis as defined in the enclosed claim 1. The articulated prosthesis is the portion, left in the patient's heart, of a related catching device.

It is also disclosed a device for repairing a tricuspid or mitral valve comprising a catching device inserted in a distended configuration into an interventional catheter.

Further embodiments are defined in the enclosed claims. The claims as filed are integral part of the present description and are herein incorporated by reference.

DETAILED DESCRIPTION OF EXEMPLARY EMBODIMENTS

Figure 4:
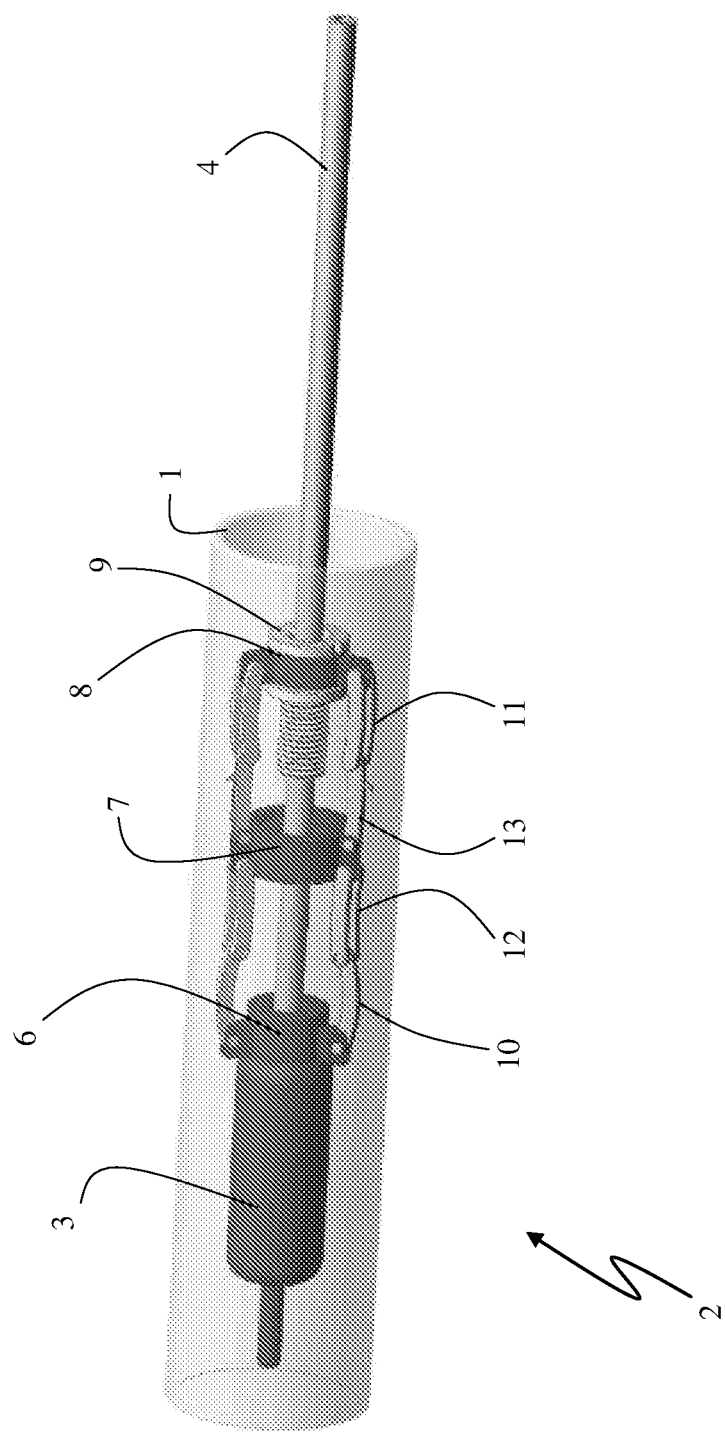
FIG. 4 depicts a device for repairing a tricuspid or mitral valve, comprising a catching device of this disclosure in a distended configuration and inserted into a catheter.
Figure 8:
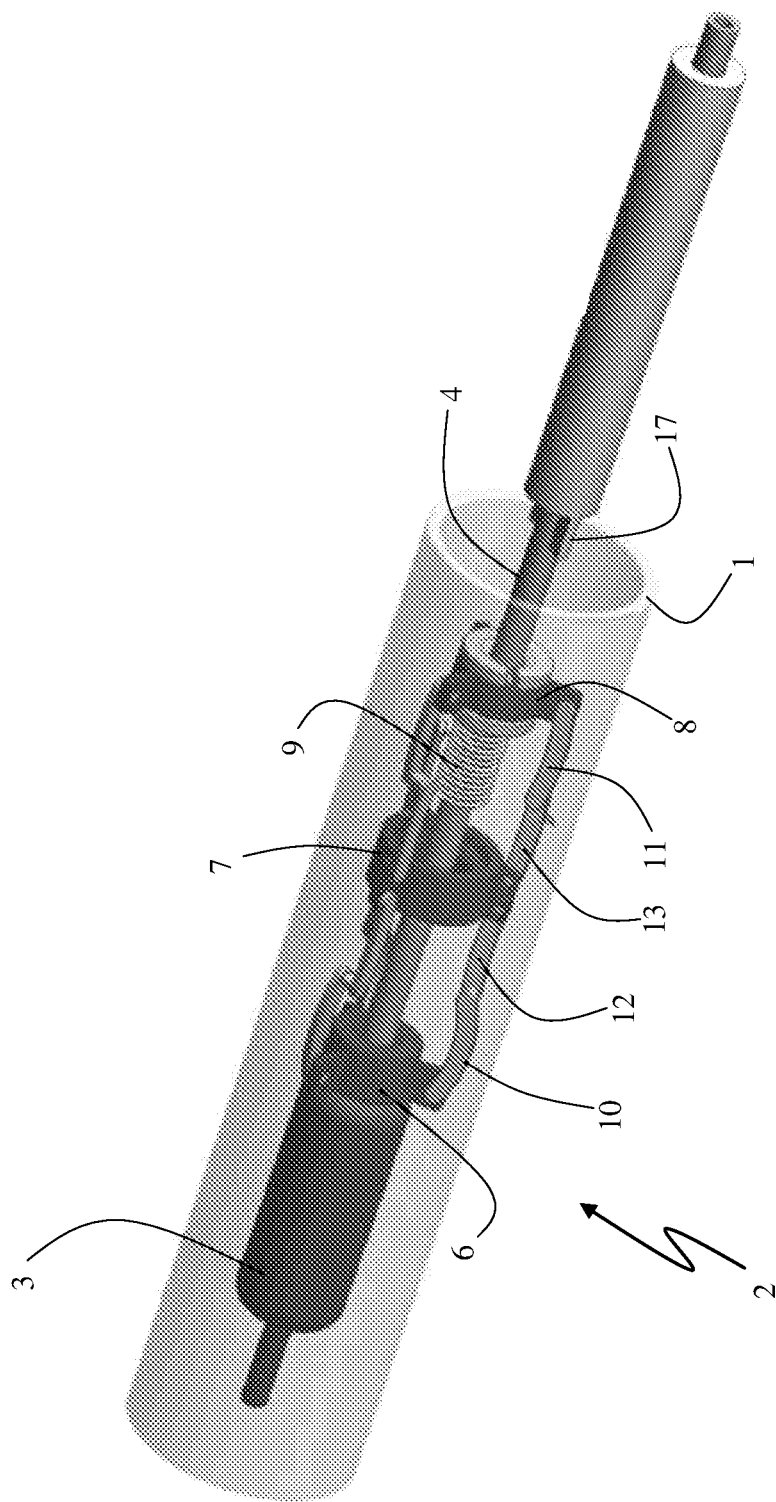
FIG. 8 depicts a device for repairing a tricuspid or mitral valve according to an alternative embodiment.

Innovative devices of this disclosure for repairing a tricuspid or mitral valve are schematically depicted in FIGS. 4 and 8. They comprise an interventional catheter 1 and a catching device 2 inserted therein in a distended configuration, for gripping the leaflets of a tricuspid or mitral valve.

In the ensuing description reference will be made to the repair of a tricuspid valve, though the same observations hold mutatis mutandis for the repair of a mitral valve. For this reason, the catching device 2 shown in the figures has three rows of rigid arms regularly disposed around circular side surfaces of the catching device in order to grip the three leaflets of a tricuspid valve. Nevertheless, the depicted catching device 2 could be made with only two rows of rigid arms for gripping the two leaflets of a mitral valve, or even with four or more rows of rigid arms for better catching the leaflets of any heart valve.

The catching device 2 shown in FIG. 4 has mainly a balloon 3, an inflation tube 4, and an articulated prosthesis 5, better illustrated in figures from 5 to 7B and from 9 to 11B, for catching the leaflets of a heart valve and for keeping them laying distended fully in the valve plane without overstretching or folding them.

Figure 5:
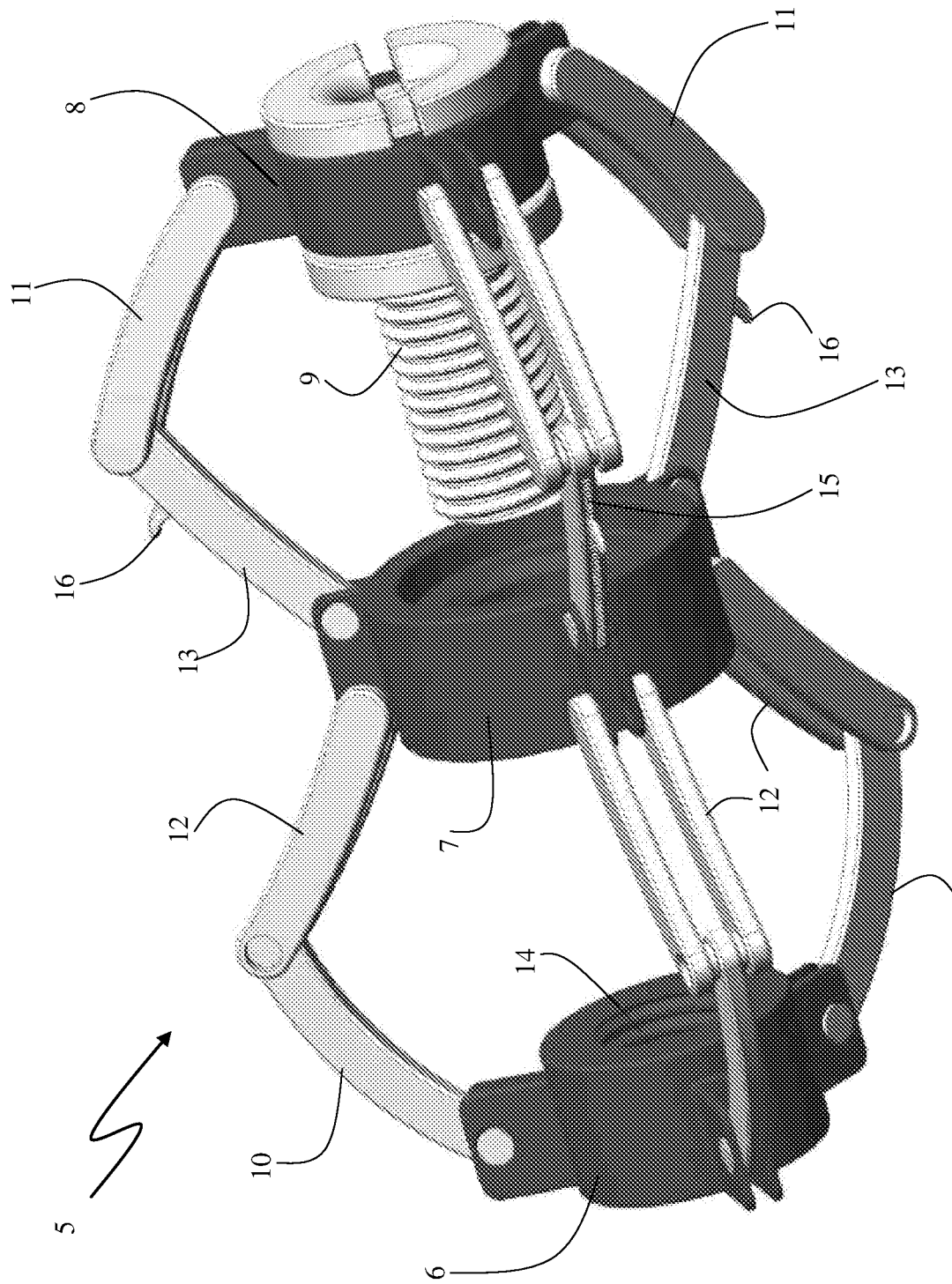
FIG. 5 depicts the articulated prosthesis of FIG. 4 in a distended configuration.
Figure 9:
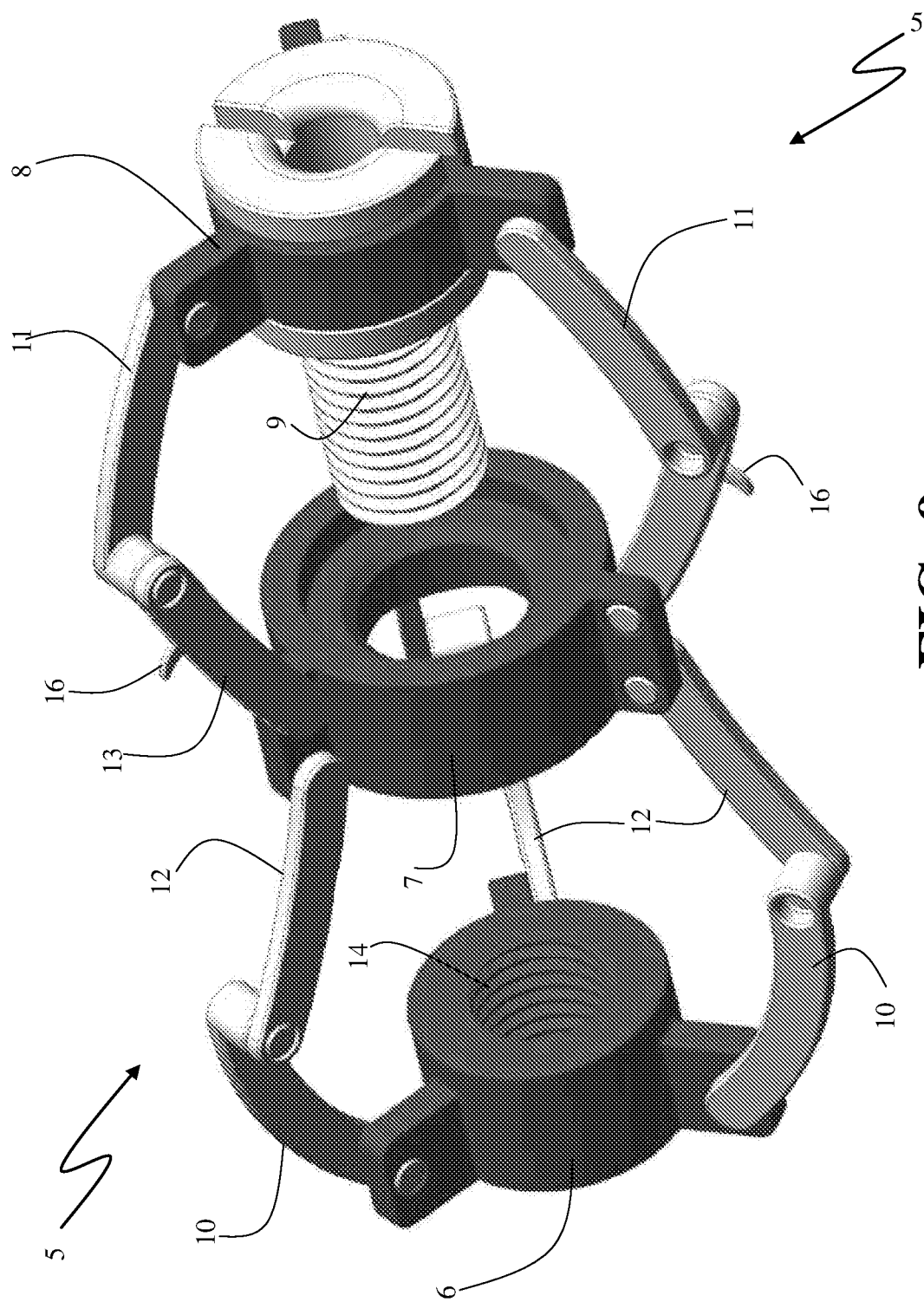
FIG. 9 depicts the articulated prosthesis of FIG. 8 in a distended configuration.
Figure 10A:
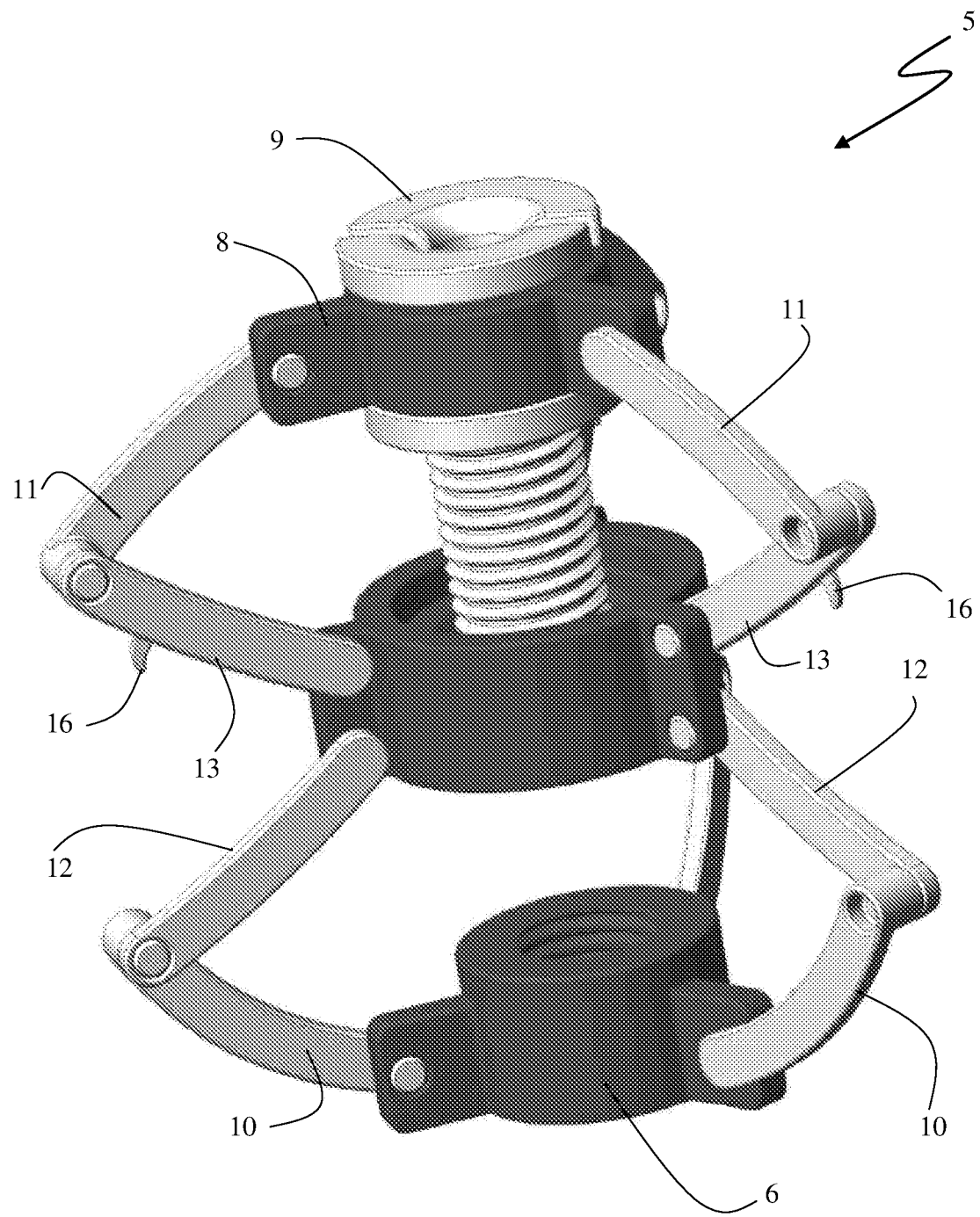
FIGS. 10A and 10B depict the articulated prosthesis of FIG. 9 in a half-extended configuration.
Figure 10B:
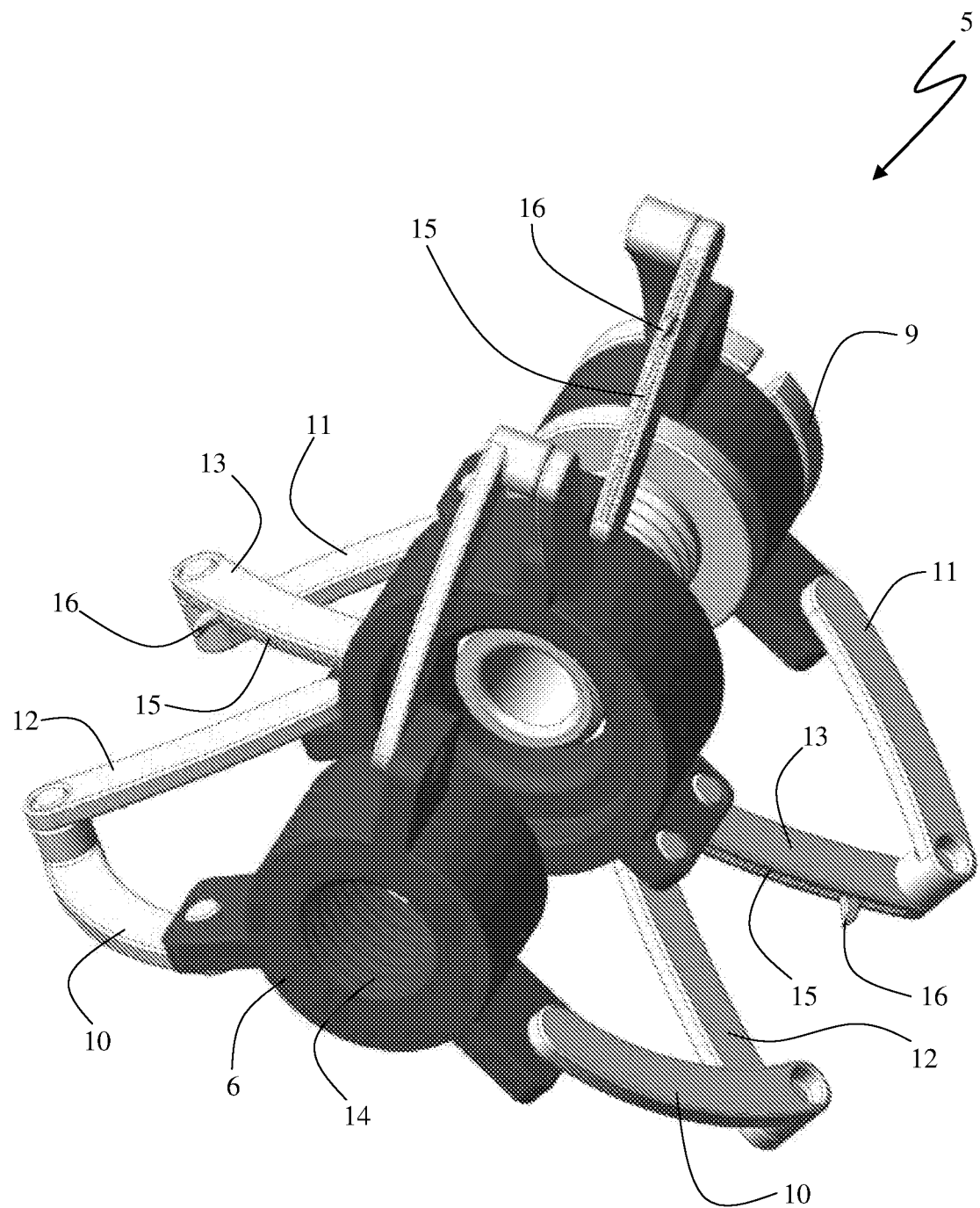

The articulated prosthesis 5 in a distended configuration is illustrated in FIG. 5 (FIG. 9). It comprises:
  a distal annular cylindrical portion 6,
  a central annular cylindrical portion 7,
  a proximal annular cylindrical portion having a cylindrical collar 8 and a screw 9 engaged into the collar 8 and supported thereby so as to be free to rotate along a longitudinal axis,
  a first plurality of rigid arms 10 hinged to an outer side surface of the distal annular cylindrical portion 6,
  a second plurality of rigid arms 11 hinged to an outer side surface of the collar 8,
  a third plurality of rigid arms 12 each of which is hinged to an outer side surface of the central annular cylindrical portion 7, from one end, and to a corresponding end of a rigid arm 10 from the opposite end,
  a fourth plurality of rigid arms 13 each of which is hinged to an outer side surface of the central annular cylindrical portion 7, from one end, and to a corresponding end of a rigid arm 11 from the opposite end.

Figure 7A:
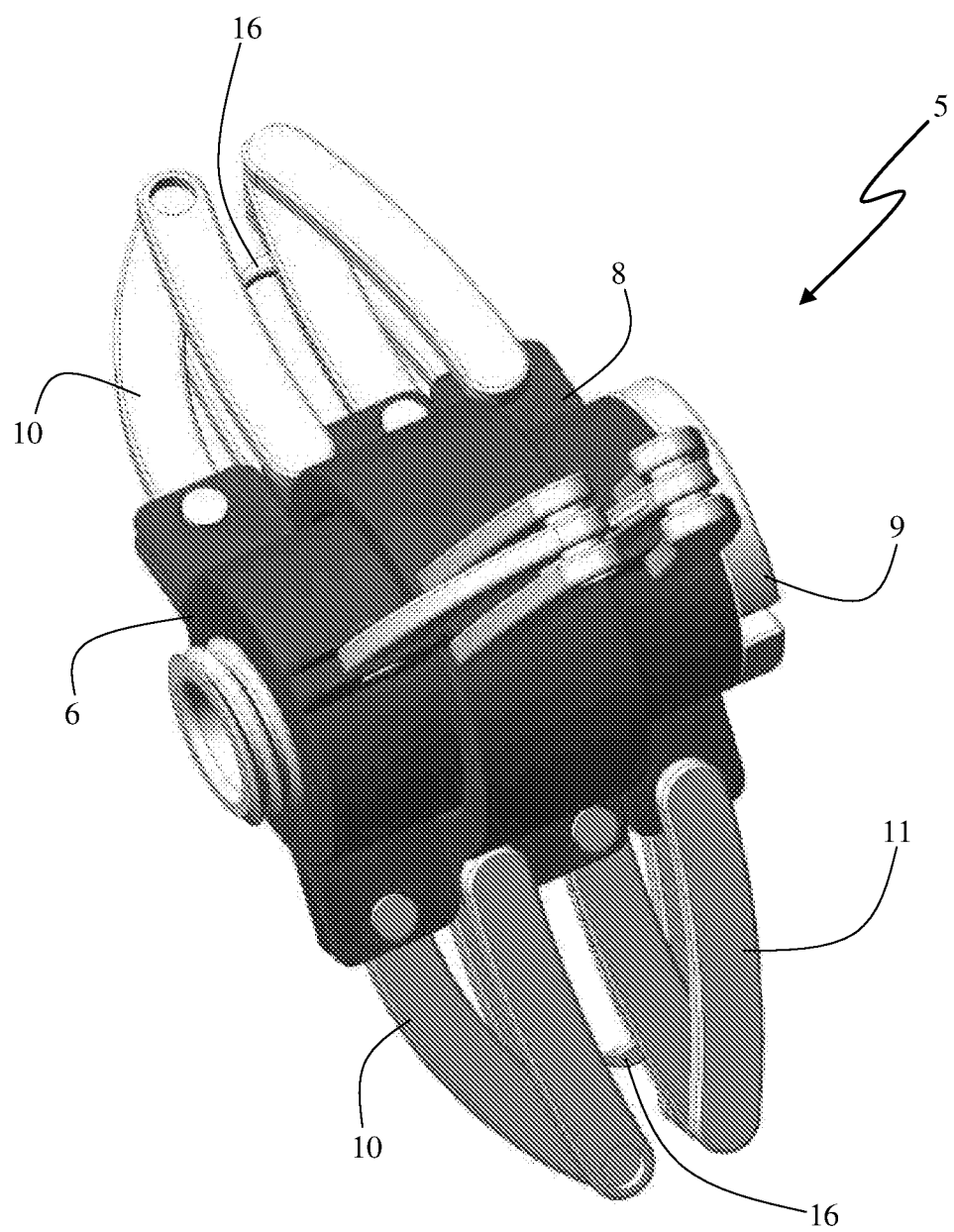
FIGS. 7A and 7B depict the articulated prosthesis of FIG. 5 in an extended configuration with the screw of the proximal portion tightly screwed into the distal portion.
Figure 7B:
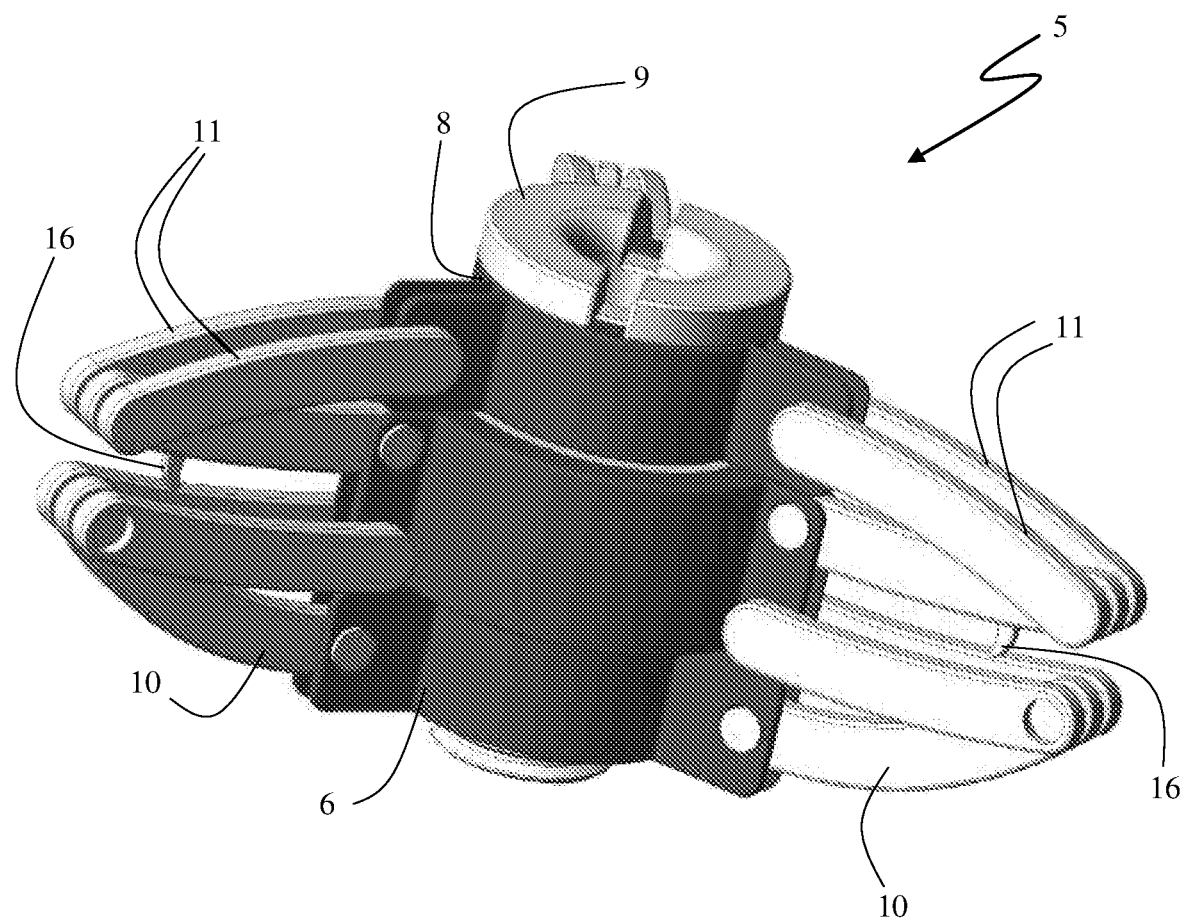
Figure 11A:
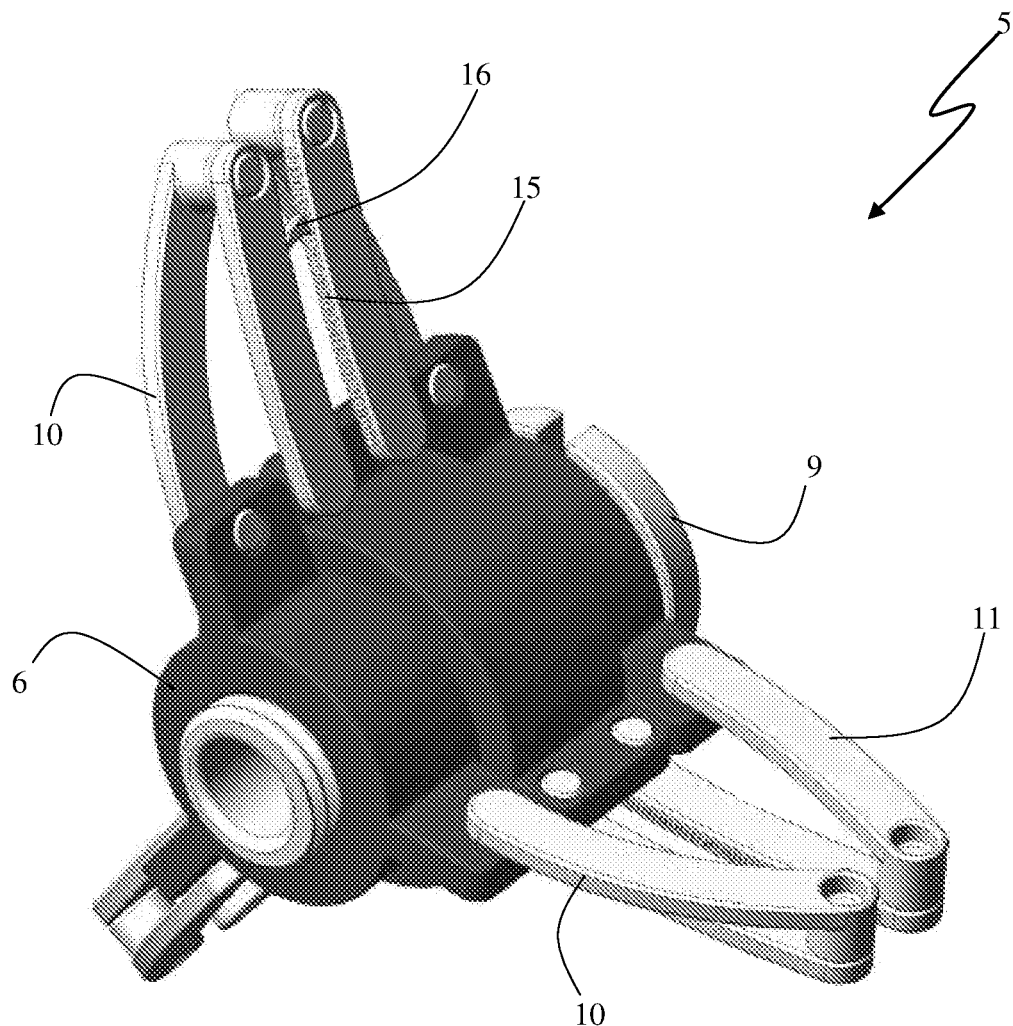
FIGS. 11A and 11B depict the articulated prosthesis of FIG. 9 in an extended configuration with the screw of the proximal portion tightly screwed into the distal portion.
Figure 11B:
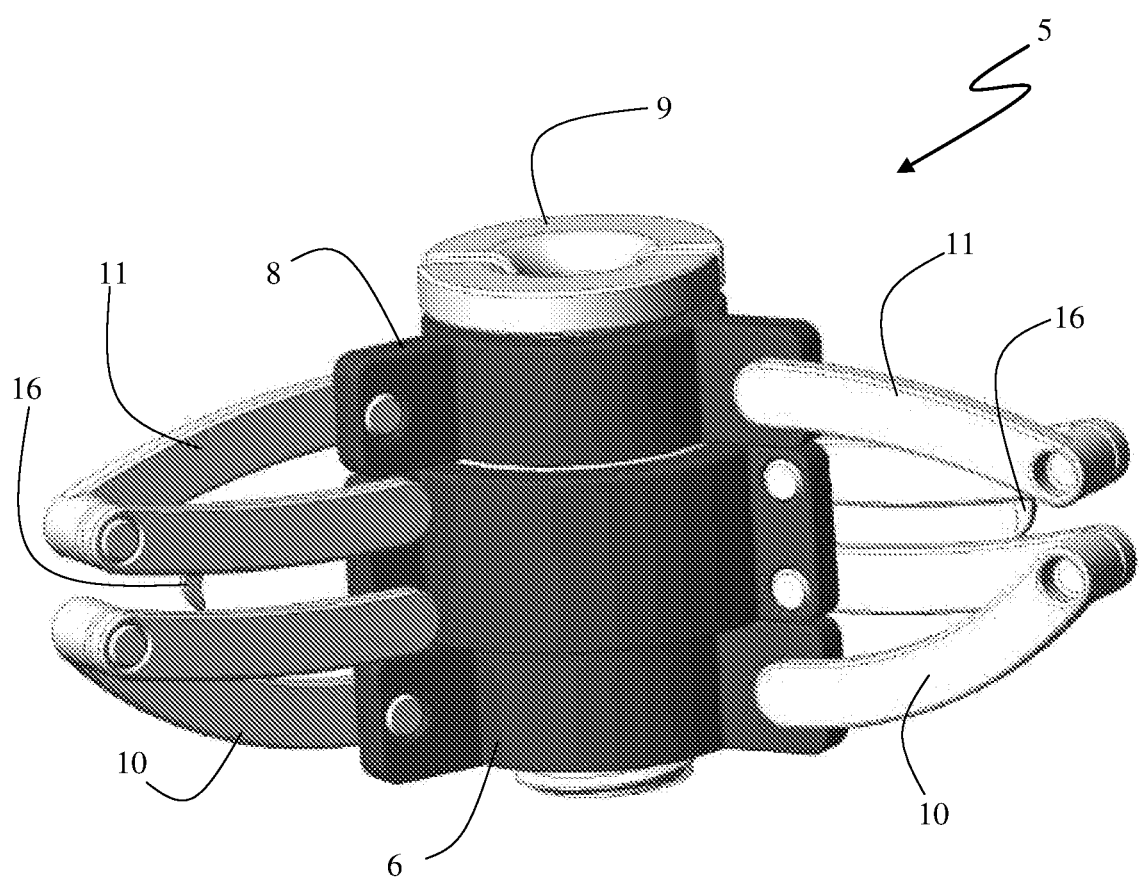

The distal portion 6 has an internal screw thread 14 configured to engage with the screw 9 when the articulated prosthesis 5 passes from the distended configuration of FIG. 5 to the expanded configuration of FIGS. 7A and 7B (FIGS. 11A and 11B). The central portion 7 has a through hole to let the screw 9 pass therethrough. By screwing the screw 9 in the distal portion 6, the rigid arms 10, 11, 12, 13 are extended and the arms 12 and 13 grab between them the leaflets of the heart valve. When the screw 9 is tightened in the screw thread 14, the articulated prosthesis 5 holds firmly the heart valve leaflets and is left in place as a prosthesis, that may be easily removed by a surgeon if necessary.

In order to provide a good gripping of the leaflets, at least one of the facing arms 12 and 13 has a knurling 15 and a pointed projection 16 configured to spike the tissue of the corresponding leaflet. In the depicted embodiment only the rigid arms 13 are provided with the knurling 15 and the projection 16, though they may be realized also on some or all of the rigid arms 12 for catching even better the leaflets of the heart valve.

The arms shall be made of rigid material in order to catch firmly the leaflets and preventing them from slipping out.

Figure 1:
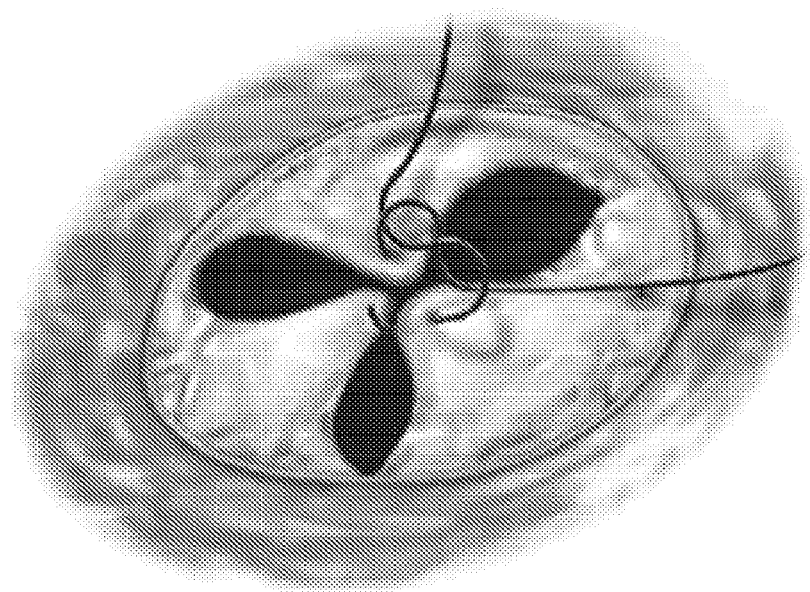
FIG. 1 schematically depicts a typical configuration of a tricuspid valve after the so-called "clover technique" surgical intervention.
Figure 2:
FIG. 2 depicts a prior fastener for leaflets of a mitral or tricuspid valve.

The relative position of the pointed projection 16 on the rigid arm 13 may be established to spike a heart valve leaflet as close as possible to the tip, as shown in FIG. 1 and as it would be done in the classic surgical technique. This result may be attained for example by placing the pointed projections 16 at about the middle of the rigid arm 13.

Figure 3:
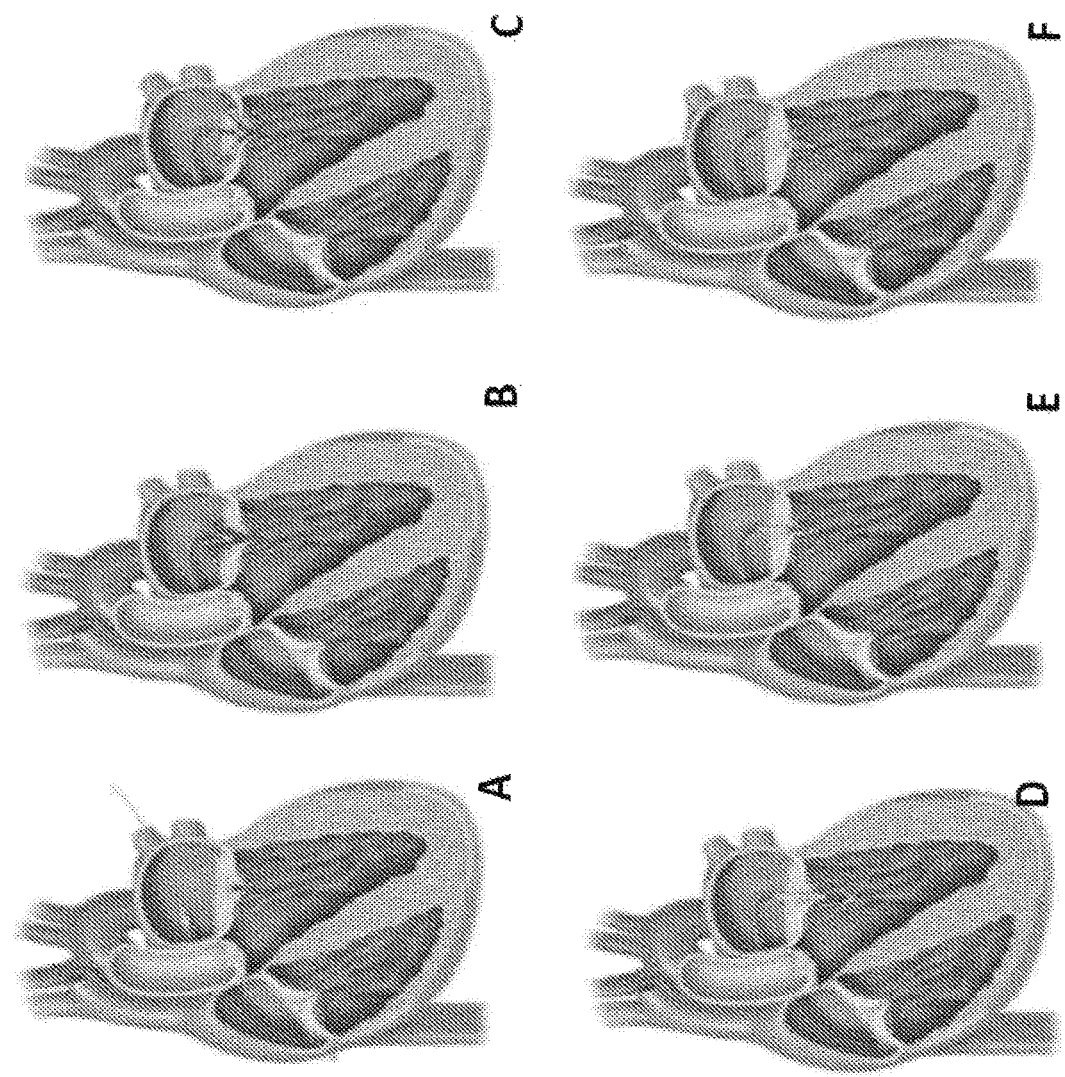
FIG. 3 shows various steps for implanting the so-called MITRA CLIP™ fastener to leaflets of a heart valve.

The catheter 1 is adapted to be inserted into the heart of a patient passing throughout a vein, as shown in FIG. 3 and commonly done for the prior MITRA CLIP™ device, or from an incision in the chest of a patient. An inflation tube 4, made of a flexible material, functionally connected to an inflatable balloon 3, is equipped with screwing means 17 (shown in the FIG. 8 only) for pushing the whole catching device 2 to exit from the catheter when close to the heart valve to be repaired and for screwing the screw 9 into the distal portion 6 of the articulated prosthesis. These screwing means may be in the form of a screwing tube 17 threaded around the inflation tube 4 and having an end portion shaped as the tip of a screwdriver to engage with the slit of the screw 9.

In a distended configuration, the catching device is conveyed to the hearth valve to be repaired and the catheter is pulled back and/or the tube 4 is pushed forward so as to place the distal portion 6 and the arms 10, 12 below a valve plane to raise the leaflets, and the arms 13 and 11 and the proximal part, comprising the collar 8 and the screw 9, above the valve plane. The balloon 3 is inflated through the inflation tube 4 and is dragged backwards so as to pull the distal portion 6 towards the screw 9. The rigid arms 10, 11, 12 and 13 protrude radially (FIGS. 6A and 6B) the closer the distal portion 6 is to the screw 9, and in the shown configuration the arms 12 start to come into contact with the hanging leaflets of the heart valve.

Figure 6A:
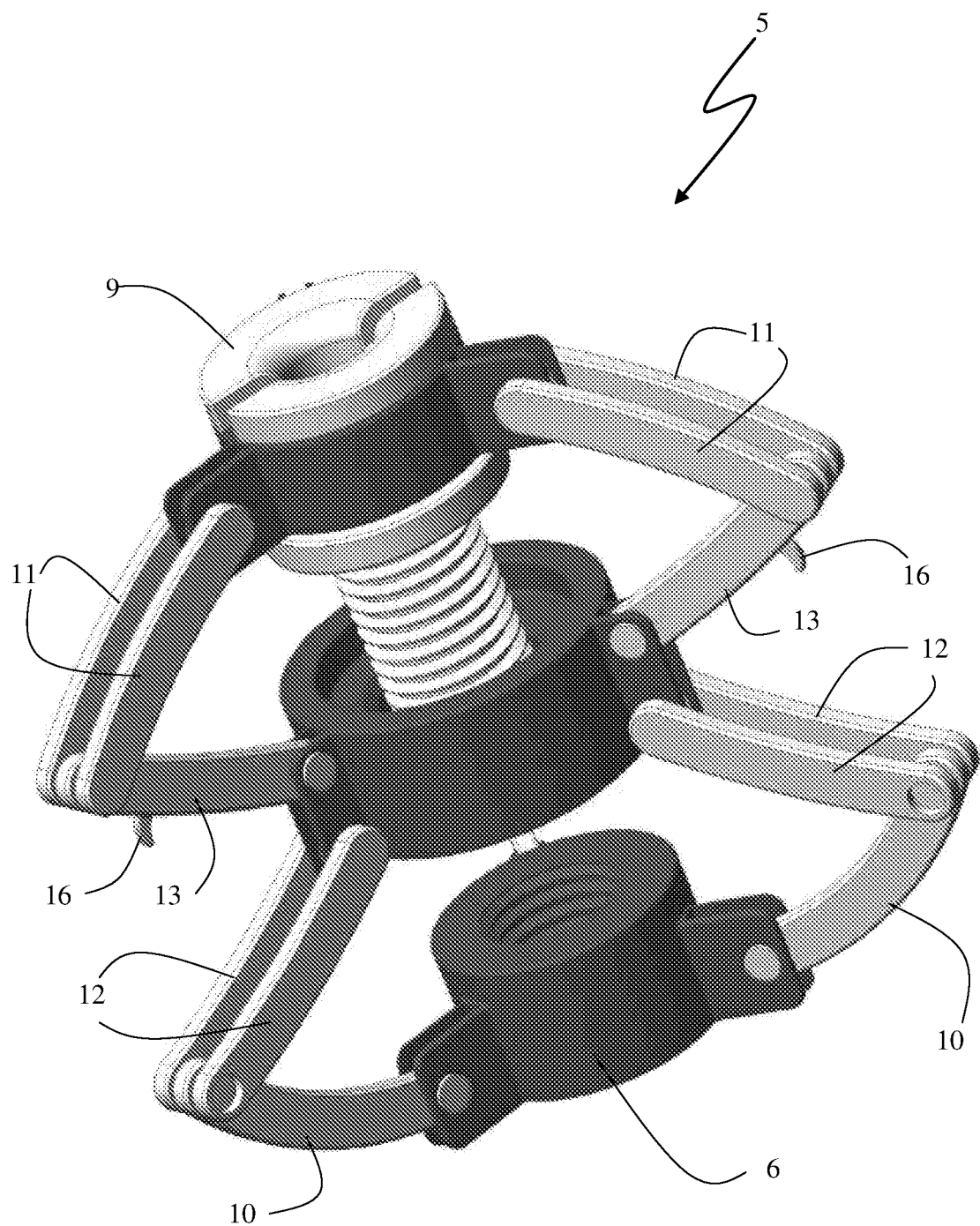
FIGS. 6A and 6B depict the articulated prosthesis of FIG. 5 in a half-extended configuration.
Figure 6B:
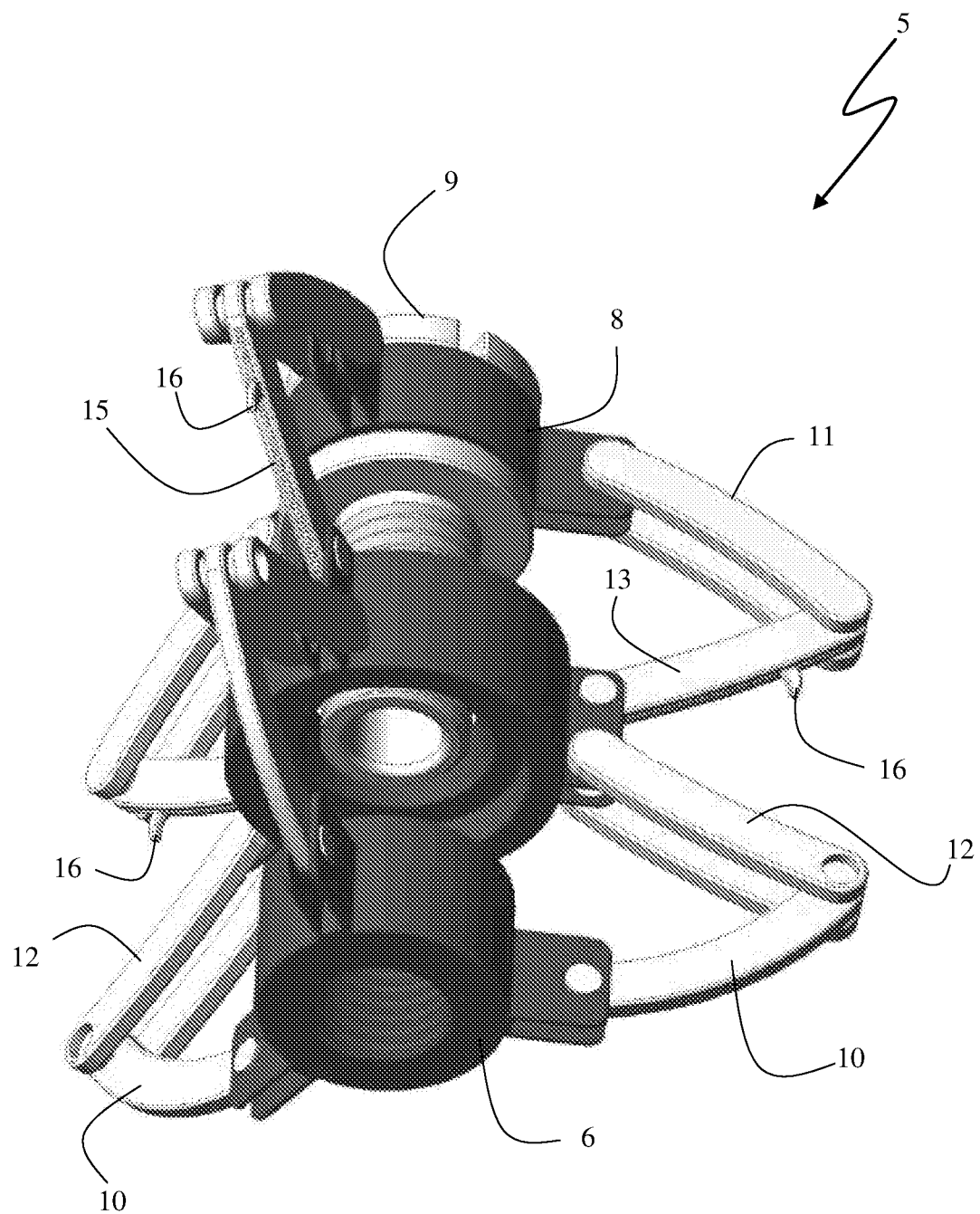

According to a preferred embodiment, the facing rigid arms 12 are concave as shown in FIGS. 6A and 6B so as to raise the valve leaflets starting from their portions close to the perimeter of the valve orifice.

By dragging back further the balloon 3, the screw 9 comes into contact with the internal screw thread 14 of the distal portion 6. It is thus possible to regulate the squeezing force on the valve leaflets between the rigid arms 12 and 13 depending on the thickness of the valve leaflets, by tightening more or less deeply the screw 9 into the distal portion 14. When the articulated prosthesis 5 is in the extended configuration, the valve leaflets (not shown) are trapped between the facing rigid arms 12 and 13. According to the embodiment shown in FIGS. 7A and 7B, each leaflet is caught between a pair of parallel rigid arms 12 and a single rigid arm 13. The parallel rigid arms 12 are staggered in respect to the rigid arm 13 to grasp the leaflets as a paper clip keeping them distended in the valve plane and not overstretched.

Thanks to the grip of the knurling 15 and to the pointed projections 16, the leaflets are firmly held by the rigid arms 12, 13 and cannot slip out.

There will be a sufficient light between the leaflets as in the common surgical "clover technique", thus the risk of causing stenosis is reduced.

When the screw 9 is firmly engaging the distal portion 6, the balloon 3 is deflated and is dragged back into the interventional catheter 1 passing throughout the articulated prosthesis 5, which is left in the patient's heart.

According to an alternative embodiment shown in figures from 8 to 11B, each leaflet of a tricuspid valve is pinched between a single rigid arm 12 and a facing rigid arm 13. The functioning of the shown device is substantially the same as for the embodiment illustrated in figures from 4 to 7B.

Preferably, as in the embodiment of figures from 4 to 7B, the rigid arms 12 and 13 are not hinged together around a same axis on the central portion 7 for preventing them from functioning as scissors and avoiding the risk of cutting the valve leaflet instead of squeezing/pinching it.

Another advantage of the catching mechanism of this disclosure is the fact that it is possible to substitute the articulated prosthesis installed in a patient's heart, if required, by executing the above operations in the reverse order. More in detail, the articulated prosthesis may be unmounted from the patient's heart through the following operations:

- inserting a deflated balloon 3 through the proximal portion up to exit from the distal portion 6;
- inflating the balloon 3 and abutting it against the distal portion 6;
- unscrewing the screw 9 from the distal portion 6 using the screwing means 17 and allowing the articulated prosthesis 5 to assume a distended configuration; and
- finally inserting the distended articulated prosthesis into a catheter by pulling the inflation tube 4.

The articulated prosthesis 5 will be made of bio-compatible materials adapted for heart prosthesis to be implanted into a patient's heart.

The invention claimed is:

1. An articulated prosthesis for a tricuspid or a mitral valve, comprising:
    a distal annular portion, a central annular portion and a proximal annular portion;
    a first plurality of rigid arms hinged to an outer side surface of said distal annular portion;
    a second plurality of rigid arms hinged to an outer side surface of said proximal annular portion;
    a third plurality of rigid arms each of which has a respective first end hinged to an outer side surface of said central annular portion, and a respective second end opposite to said respective first end hinged to a corresponding second end of a rigid arm of said first plurality;
    a fourth plurality of rigid arms each of which has a respective first end hinged to an outer side surface of said central annular portion, and a respective second end opposite to said respective first end hinged to a corresponding second end of a rigid arm of said second plurality;
    at least one rigid arm of said rigid arms of said third plurality and/or at least one rigid arm of said rigid arms of said fourth plurality having a respective knurling defined on a respective catching surface, the catching surfaces of the rigid arms of said fourth plurality also defining pointed projections configured for spiking leaflets of said tricuspid or mitral valve;
    said distal annular portion having an internal screw thread, said proximal annular portion having:
    a cylindrical collar on a side surface of which said second plurality of rigid arms is hinged, and
    a screw engaged into said collar and supported thereby so as to be free to rotate along a longitudinal axis of the screw, the screw being configured to engage with said internal screw thread,
    said central annular portion defining a through hole for letting said proximal annular portion pass through;
    said articulated prosthesis being movable from a distended configuration, in which all said rigid arms hinged in correspondence of their ends are distended along a longitudinal direction of said articulated prosthesis, to an expanded configuration, in which all said rigid arms hinged in correspondence of their ends are distended along a radial direction in a valve plane of said tricuspid or mitral valve, wherein said valve plane is transverse with respect to said longitudinal direction of the articulated prosthesis, and in which said proximal annular portion rests in the through hole of said central annular portion and is engaged with said distal annular portion, the rigid arms of said third plurality and of said fourth plurality being configured to hold therebetween said leaflets of said tricuspid or mitral valve, with said pointed projections spiking said leaflets held between the rigid arms of said third plurality and of said fourth plurality, when said articulated prosthesis is in the expanded configuration;
    wherein said pointed projections are configured to spike said valve leaflets trapped between the rigid arms of said third plurality and of said fourth plurality when the articulated prosthesis is in the extended configuration, so as the valve leaflets are held distended in the valve plane without being folded by the rigid arms of said third plurality and of said fourth plurality and at the same time the valve leaflets are spiked by said pointed projections and a light is left between the valve leaflets;
    wherein said respective catching surfaces of said rigid arms of the third plurality are concave to define a concavity of said respective catching surfaces oriented towards said rigid arms of the fourth plurality when the articulated prosthesis is in the expanded configuration;
    a number of said rigid arms of said second plurality and said third plurality is twice a number of rigid arms of said first plurality and said fourth plurality, each rigid arm of said fourth plurality is hinged together with a respective first pair of parallel rigid arms composed of two parallel rigid arms of said second plurality, each rigid arm of said third plurality is hinged together with a respective second pair of parallel rigid arms composed of two parallel rigid arms of said first plurality;
    wherein each rigid arm of said fourth plurality of arms faces a respective pair of rigid arms of the third plurality and no rigid arm of said third plurality is in more than one pair of the rigid arms of the third plurality, and
    wherein said rigid arms of said respective pair of rigid arms of the third plurality are offset circumferentially with respect to the facing rigid arm of said fourth plurality so as said pointed projections are configured to spike the valve leaflets between respective rigid arms of said pair of rigid arms of the third plurality when the articulated prosthesis is in the extended configuration.

2. The articulated prosthesis of claim 1, wherein said rigid arms of the fourth plurality are longitudinally concave to define a concavity of said rigid arms of the fourth plurality oriented in an opposite direction with respect to said rigid arms of said third plurality when the articulated prosthesis is in the expanded configuration.

\* \* \* \* \*